United States Patent
Zhang et al.

(10) Patent No.: US 11,305,124 B2
(45) Date of Patent: *Apr. 19, 2022

(54) SYSTEM AND METHOD FOR PACING PARAMETER OPTIMIZATION USING HEART SOUNDS

(71) Applicant: Medtronic, Inc., Minneapolis, MN (US)

(72) Inventors: Xusheng Zhang, Shoreview, MN (US); Jeffrey M. Gillberg, Coon Rapids, MN (US); Thomas J. Mullen, Andover, MN (US)

(73) Assignee: Medtronic, Inc., Minneapolis, MN (US)

( * ) Notice: Subject to any disclaimer, the term of this patent is extended or adjusted under 35 U.S.C. 154(b) by 151 days.

This patent is subject to a terminal disclaimer.

(21) Appl. No.: 16/551,412

(22) Filed: Aug. 26, 2019

(65) Prior Publication Data

US 2019/0381315 A1     Dec. 19, 2019

Related U.S. Application Data

(63) Continuation of application No. 15/589,868, filed on May 8, 2017, now Pat. No. 10,391,316, which is a
(Continued)

(51) Int. Cl.
*A61N 1/362* (2006.01)
*A61N 1/372* (2006.01)
(Continued)

(52) U.S. Cl.
CPC ............. *A61N 1/3627* (2013.01); *A61B 7/04* (2013.01); *A61N 1/3682* (2013.01);
(Continued)

(58) Field of Classification Search
None
See application file for complete search history.

(56) References Cited

U.S. PATENT DOCUMENTS 4,546,777 A   10/1985  Groch
5,554,177 A    9/1996  Kieval
(Continued)

OTHER PUBLICATIONS

Van Bommel et al. Critical appraisal of the use of cardiac resynchronization therapy beyond current guidelines, J Am Coll Cardiol 2010, 56 (10), 754-762.
(Continued)

*Primary Examiner* — Erica S Lee
(74) *Attorney, Agent, or Firm* — Shumaker & Sieffert, P.A.

(57) ABSTRACT

A medical device system and associated method predict a patient response to a cardiac therapy. The system includes for delivering cardiac pacing pulses to a patient's heart coupled to a cardiac sensing module and a cardiac pacing module for generating cardiac pacing pulses and controlling delivery of the pacing pulses at multiple pace parameter settings. An acoustical sensor obtains heart sound signals. A processor is enabled to receive the heart sound signals, derive a plurality of heart sound signal parameters from the heart sound signals, and determine a trend of each of the plurality of heart sound signal parameters with respect to the plurality of pace parameter settings. An external display is configured to present the trend of at least one heart sound parameter with respect to the plurality of pace parameter settings.

26 Claims, 6 Drawing Sheets

Related U.S. Application Data continuation of application No. 13/296,605, filed on Nov. 15, 2011, now Pat. No. 9,643,014.

(60) Provisional application No. 61/512,971, filed on Jul. 29, 2011.

(51) Int. Cl.
    *A61N 1/368* (2006.01)
    *A61N 1/365* (2006.01)
    *A61B 7/04* (2006.01)
    *A61N 1/37* (2006.01)

(52) U.S. Cl.
    CPC ....... *A61N 1/3686* (2013.01); *A61N 1/36578* (2013.01); *A61N 1/36842* (2017.08); *A61N 1/3702* (2013.01); *A61N 1/37247* (2013.01); *A61N 1/37264* (2013.01); *A61N 1/3684* (2013.01); *A61N 1/36843* (2017.08)

(56) References Cited

U.S. PATENT DOCUMENTS

| | | | |
|---|---|---|---|
| 5,683,432 A | 11/1997 | Goedeke | |
| 6,144,880 A | 11/2000 | Ding et al. | |
| 6,418,346 B1 | 7/2002 | Nelson | |
| 6,442,433 B1 | 8/2002 | Linberg | |
| 6,477,406 B1 | 11/2002 | Turcott | |
| 6,480,745 B2 | 11/2002 | Nelson | |
| 6,527,729 B1 | 3/2003 | Turcott | |
| 6,599,250 B2 | 7/2003 | Webb | |
| 6,622,045 B2 | 9/2003 | Snell et al. | |
| 6,869,404 B2 | 3/2005 | Schulhauser | |
| 6,871,088 B2 | 3/2005 | Chinchoy | |
| 7,035,684 B2 | 4/2006 | Lee | |
| 7,548,784 B2 | 6/2009 | Chinchoy | |
| 7,559,900 B2 | 7/2009 | Gillberg | |
| 7,585,279 B2 | 9/2009 | Carlson | |
| 7,682,316 B2 | 3/2010 | Anderson | |
| 7,972,275 B2 | 7/2011 | Siejko et al. | |
| 9,643,014 B2 * | 5/2017 | Zhang | A61B 7/00 |
| 10,391,316 B2 * | 8/2019 | Zhang | A61N 1/3627 |
| 2002/0161307 A1 | 10/2002 | Yu | |
| 2004/0167417 A1 | 8/2004 | Schulhauser | |
| 2006/0149328 A1 * | 7/2006 | Parikh | A61N 1/3627 607/28 |
| 2007/0093874 A1 | 4/2007 | Chirife et al. | |
| 2008/0015653 A1 | 1/2008 | Siejko et al. | |
| 2008/0103406 A1 | 5/2008 | Kameli | |
| 2008/0243202 A1 | 10/2008 | Patangay | |
| 2008/0287582 A1 | 11/2008 | Weiss | |
| 2009/0254139 A1 | 10/2009 | Bjorling | |
| 2011/0004264 A1 | 1/2011 | Siejko et al. | |
| 2011/0009760 A1 | 1/2011 | Zhang | |
| 2013/0030484 A1 | 1/2013 | Zhang et al. | |

OTHER PUBLICATIONS

Auricchio A, et al. Effect of pacing chamber and atrioventricular delay on acute systolic function of paced patients with congestive heart failure. Circulation 1999; 99; 2993-3001.

"A System and Method of a Programmer-Based Easy-to-Use Cost-Effective Pacing Parameter Optimization Tool using Heart Sounds (HS) Hemodynamic Information to Increase Therapy Response Rate", ProgrammerBasedHeartSoundsCRTOptimization.doc, Oct. 24, 2010, 9 pages.

Packer, Milton, MD., "Proposal for a New Clinical End Point to Evaluate the Efficacy of Drugs and Devices in the Treatment of Chronic Heart Failure", Journal of Cardiac Failure, vol. 7, No. 2, Jun. 2001, pp. 176-182 pages.

* cited by examiner

SYSTEM AND METHOD FOR PACING PARAMETER OPTIMIZATION USING HEART SOUNDS

CROSS-REFERENCE TO PRIORITY APPLICATION

This application is a continuation of U.S. Pat. No. 9,643,014 entitled "A SYSTEM AND METHOD FOR PACING PARAMETER OPTIMIZATION USING HEART SOUNDS" (now allowed), which claims priority to U.S. provisional application No. 61/512,971, filed Jul. 29, 2011; which is incorporated by reference herein.

FIELD OF THE DISCLOSURE

The disclosure relates to a medical device system and associated method for optimizing cardiac therapy pacing parameters based on heart sounds.

BACKGROUND

Cardiac resynchronization therapy (CRT) is one therapy used to treat heart failure (HF) patients. During CRT, pacing pulses are delivered to one or more heart chambers to restore synchrony of the heart chambers. Guidelines for selecting patients for CRT have been established, e.g. New York Heart Association (NYHA) classification III to IV, left ventricular ejection fraction (LVEF) 35% or less, and a wide QRS complex of 120 ms or more. Despite these guidelines, not all patients benefit from CRT. Some patients, "responders," present clinically significant hemodynamic improvement to CRT therapy while others are considered "non-responders" presenting little or no improvement. Because of the varied response to CRT between patients meeting current guidelines, patient selection for CRT continues to be challenging to clinicians.

Once a patient is selected for a pacing therapy, optimizing timing of pacing parameters is important in achieving therapeutic benefit of a pacing therapy, or at least preventing unintentional deleterious hemodynamic effects of a pacing therapy. Pacing timing control parameters include the atrial-ventricular (AV) interval used during single chamber ventricular pacing, during dual chamber (atrial and ventricular) pacing, and multi-chamber pacing, and the intra-ventricular (VV) interval used during biventricular or multi-chamber pacing. The AV interval is a pacing control time interval started upon sensing an atrial event (P-wave) or delivering an atrial pacing pulse (A-pace). Upon expiration of the AV interval, the pacing device delivers a ventricular pacing pulse (V-pace) if an intrinsic ventricular event (R-wave) is not sensed during the AV interval. Similarly, the VV interval is used to control the timing of a ventricular pacing pulse following a programmed W interval after a paced or sensed R-wave occurring in the opposite ventricular chamber.

Echocardiography continues to be a "gold standard" for optimizing pacing timing parameters. Echocardiography, however, tends to be a costly and time-consuming procedure which requires specially trained sonographers to perform. Other methods for monitoring hemodynamic performance of the heart typically require invasive techniques such as cardiac catheterization for measuring left ventricular (LV) pressure, cardiac output or other standard hemodynamic measurements. As such, the frequency that such techniques can be used to determine the best pacing parameters for an individual patient are limited due to time, cost, burden on the patient, and/or inherent risks associated with invasive methods. It would be desirable for a clinician to know with a relatively high certainty beforehand whether a patient will be responsive to a given therapy and how best to manage the therapy to avoid costly, time-consuming and invasive procedures.

Other methods proposed for selecting CRT patients and optimizing CRT therapy include measuring the QRS width and performing adjustments to cause a narrowing of the QRS width. This technique assumes that a wider QRS width indicates greater ventricular dyssynchrony and a narrowing of the QRS width will be associated with improved ventricular synchrony. In a significant number of patients, however, electrical dyssynchrony and mechanical dyssynchrony do not strongly correlate. As such, patient selection and optimization based on QRS width may have limited utility.

A need remains, therefore, for a medical device system and associated method for optimizing pacing parameters using low-cost and non-invasive methods which improve patient benefit to cardiac pacing therapies for treating heart failure.

DETAILED DESCRIPTION

In the following description, references are made to illustrative embodiments. It is understood that other embodiments may be utilized without departing from the scope of the disclosure. As used herein, the term "module" refers to an application specific integrated circuit (ASIC), an electronic circuit, a processor (shared, dedicated, or group) and memory that execute one or more software or firmware programs, a combinational logic circuit, or other suitable components that provide the described functionality.

Figure 1:
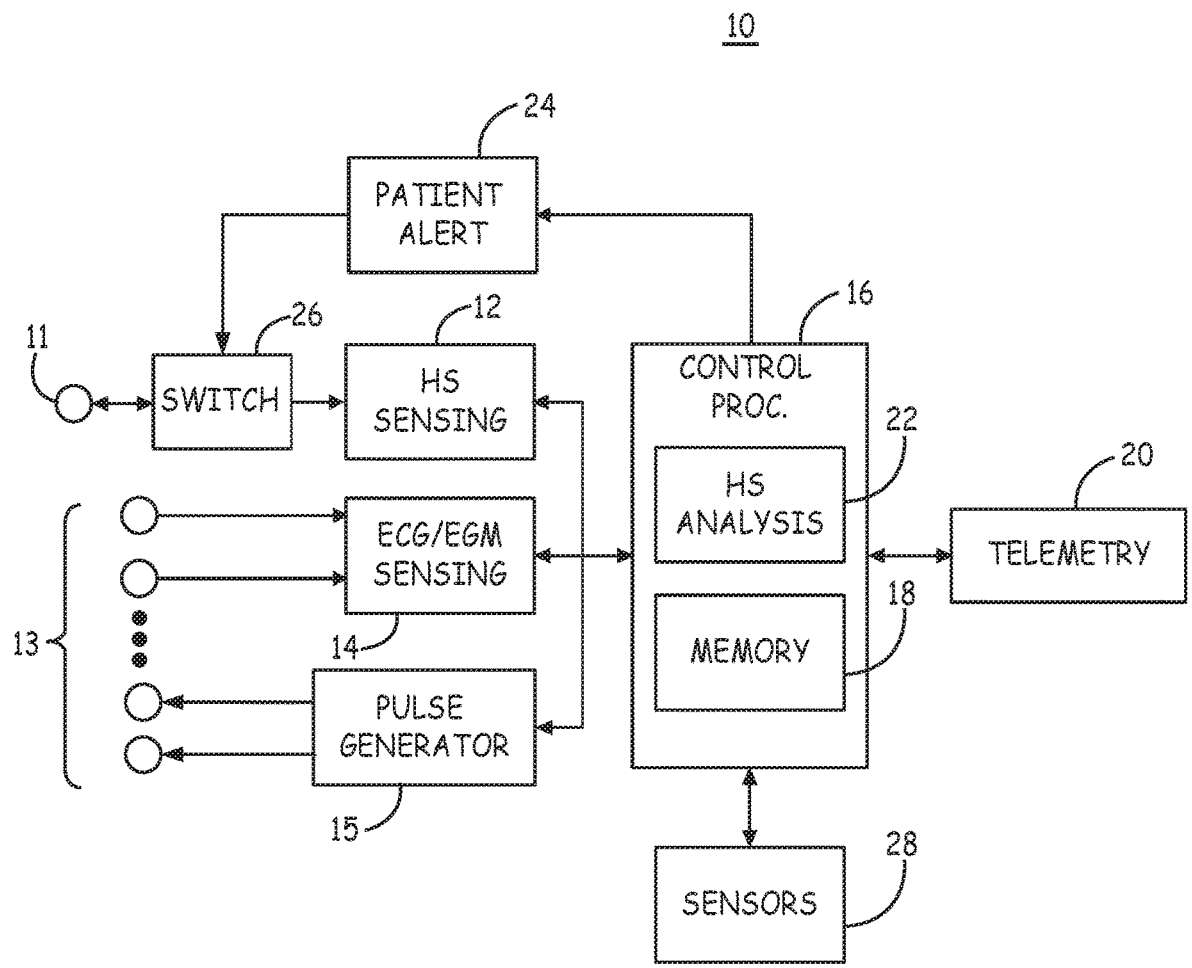
FIG. 1 is a functional block diagram of an implantable medical device (IMD) system for acquiring heart sounds and delivering a cardiac pacing therapy for treating heart failure according to one embodiment.

FIG. 1 is a functional block diagram of an IMD system 10 for acquiring heart sounds and delivering a cardiac pacing therapy for treating heart failure according to one embodiment. IMD 10 includes a heart sound (HS) sensing module 12 coupled to an acoustical sensor 11 responsive to heart sounds, cardiac signal sensing circuitry 14 and pulse generator 15 both coupled to electrodes 13, control processor 16 and associated memory 18, and telemetry circuitry 20. HS sensing module 12 receives signals from an acoustical sensor 11 for sensing heart sounds which are provided to control processor 16 for optimizing CRT pace parameters based on heart sounds.

Physicians are particularly familiar with evaluating heart sounds as part of a basic physical examination, and a stethoscope is a standard component in a physician's diagnostic tool box. Using a heart sound sensor as a component of a medical device system for automatically optimizing CRT pace parameters will enable clinicians to quickly obtain an overview of the patient's hemodynamic response to varying pace parameters and gain an indication of optimal parameter settings and how the therapy should be managed for the particular patient as will be further described herein.

Clinicians typically refer to four heart sounds, S1, S2, S3 and S4. As will be described herein, the amplitudes and/or relative time intervals of one or more of the S1 through S4 heart sounds can be useful in optimizing a patient's hemodynamic response to CRT or other cardiac therapies that include cardiac pacing and/or neural stimulation for achieving hemodynamic benefit. The first heart sound, S1, corresponds to the start of ventricular systole. Ventricular systole begins when an action potential conducts through the atrioventricular node (AV node) and quickly depolarizes the ventricular myocardium. This event is distinguished by the QRS complex on the ECG. As the ventricles contract, pressure in the ventricles begins to rise, causing abrupt closure of the mitrel and tricuspid valves between the ventricles and atria as ventricular pressure exceeds atrial pressure. This valve closure generates S1. S1 generally has a duration of about 150 ms and a frequency on the order of 20 to 250 Hz. The amplitude of S1 may provide a surrogate measurement of LV contractility. Thus, an increase in S1 amplitude positively correlates with an improvement in LV contractility.

Separation of the closure of the mitrel and tricuspid valves due to ventricular dyssynchrony can be observed as separate M1 and T1 peaks in the S1 signal. Merging of the M1 (mitral valve closure sound) and the T1 (tricuspid valve closure sound) can be used as an indication of improved ventricular synchrony.

Left ventricular pressure (LVP) rises dramatically following the QRS complex of the ECG and closure of the mitrel valve and continues to build during ventricular systole until the aortic and pulmonary valves open, ejecting blood into the aorta and pulmonary artery. Ventricular contraction continues to cause blood pressure to rise in the ventricles and the aorta and pulmonary artery during the ejection phase. As the contraction diminishes, blood pressure decreases until the aortic and pulmonary valves close. The second heart sound, S2, is generated by the closure of the aortic and pulmonary valves, near the end of ventricular systole and start of ventricular diastole. S2 is therefore correlated to diastolic pressure in the aorta and the pulmonary artery. S2 generally has a duration of about 120 ms and a frequency on the order of 25 to 350 Hz. The time interval between S1 and S2, i.e. S1-S2 time interval represents the systolic time interval (STI) corresponding to the ventricular isovolumic contraction (pre-ejection) and ejection phase of the cardiac cycle. This S1-S2 time interval provides a surrogate measurement for stroke volume.

One method used by clinicians for optimizing the AV interval during CRT involves pulsed Doppler echocardiography and adjusting the AV interval to increase the separation of the A-wave and the E-wave without A-wave truncation. The E-(early) wave and the A-(atrial) wave represent the measurement of blood flow velocity across the mitrel valve, with the E-wave occurring during passive filling of the ventricle and the A-wave occurring during active ventricular filling due to the atrial contribution or "atrial kick" during atrial systole. Greater separation of the E-wave and A-wave is thought to improve ventricular filling, when truncation of the A-wave due to onset of ventricular contraction is avoided. The occurrence of a sudden change in the timing of S2 relative to a ventricular sensed event (R-wave) or ventricular pacing pulse is used as a surrogate of the measurement of maximum time separation of the E-wave and A-wave without A-wave truncation in one embodiment as described in greater detail below.

The third heart sound, S3, is associated with early, passive diastolic filling of the ventricles, and the fourth heart sound, S4, is associated with late, active filling of the ventricles due to atrial contraction. The third sound is generally difficult to hear in a normal patient using a stethoscope, and the fourth sound is generally not heard in a normal patient. Presence of the third and fourth heart sounds during an examination using a stethoscope may indicate a pathological condition. The S3 and S4 heart sounds may be used in optimizing pace parameters as they relate to diastolic function of the heart. Generally, these sounds would be minimized or disappear when an optimal pace parameter is identified. Other aspects of the S1 through S4 heart sounds and timing thereof that may be useful in cardiac pace parameter optimization are described in the above-incorporated '260 application.

HS sensing module 12 is configured to receive analog signals from sensor 11 for sensing one or more of these heart sounds. For example, HS sensing module 12 may include one or more "channels" configured to particularly sense a specific heart sound based on frequency, duration, and timing of the heart sounds. For example, ECG/EGM sensing circuitry 14 may be used by control processor 16 to set HS sensing windows used by HS sensing module 12 for sensing the heart sounds. HS sensing module 12 may include one or more sense amplifiers, filters and rectifiers for optimizing a signal to noise ratio of heart sound signals. Separate and unique amplification and filtering properties may be provided for sensing each of the S1 through S4 sounds to improve signal quality as needed.

In various embodiments, acoustical sensor 11 may be implemented as a microphone or a 1-, 2- or 3-axis accelerometer. In one embodiment, acoustical sensor 11 is implemented as a piezoelectric crystal mounted within an implantable medical device housing and responsive to the mechanical motion associated with heart sounds. The piezoelectric crystal may be a dedicated HS sensor or may be used for multiple functions. In the illustrative embodiment shown, acoustical sensor 11 is embodied as a piezoelectric crystal that is also used to generate a patient alert signal in the form of a perceptible vibration of the IMD housing. Upon detecting an alert condition, control processor 16 causes patient alert control circuitry 24 to generate an alert signal by activating the piezoelectric crystal.

Switching circuitry 26 is used to control whether the piezoelectric crystal is used in a "listening mode" to sense HS signals by HS sensing circuitry 12 or in an "output mode" to generate a patient alert. During patient alert generation, HS sensing circuitry 12 is temporarily decoupled from acoustical sensor 11 by switching circuitry 26.

Examples of other embodiments of acoustical sensors that may be adapted for implementation with the techniques of the present disclosure are generally described in U.S. Pat. No. 4,546,777 (Groch, et al.), U.S. Pat. No. 6,869,404 (Schulhauser, et al.), U.S. Pat. No. 5,554,177 (Kieval, et al.), and U.S. Pat. No. 7,035,684 (Lee, et al.), all of which patents are hereby incorporated by reference in their entirety. Practice of the methods and techniques described herein are not limited to a particular type of acoustical sensor. Acoustical sensor 11 may be any implantable or external sensor responsive to one or more of the heart sounds generated as described in the foregoing and thereby produces an electrical analog signal correlated in time and amplitude to the heart sounds. The analog signal may be then be processed, which may include digital conversion, by HS sensing module 12 to obtain HS parameters, such as amplitudes or relative time intervals, as derived by HS sensing module 12 or control processor 16. The acoustical sensor 11 and HS sensing module 11 may be incorporated in an IMD capable of delivering CRT or another cardiac therapy being optimized or may be implemented in a separate device having wired or wireless communication with IMD 10 or an external programmer or computer (not shown in FIG. 1) used during a pace parameter optimization procedure as described below.

ECG/EGM sensing circuitry 14, coupled to at least one sensing electrode pair included in electrodes 13, is provided to sense cardiac signals, e.g. P-wave and/or R-wave signals attendant to the depolarization of the atria and ventricles of the heart, respectfully. Sensing circuitry 14 is coupled to electrodes 13, which may include transvenous intracardiac electrodes, epicardial electrodes, or subcutaneous/submuscular electrodes, for sensing cardiac EGM or ECG signals. ECG signals and EGM signals are referred to herein generally as "cardiac electrical signals". Cardiac electrical signals are sensed for use in timing pacing pulses delivered during HS signal recording for optimizing pace parameters. Cardiac electrical signals may additionally be used for timing sensing windows used by HS sensing module 12 for obtaining HS signals. Cardiac electrical signals may additionally or alternatively be used by control processor 16 for determining time intervals relative to sensed heart sounds and these time intervals may be used as surrogate hemodynamic parameters in pace parameter optimization. Sensed cardiac signals are also used in timing pacing pulses during therapy delivery according to programmed pacing intervals, such as programmed AV interval and VV interval.

Pulse generator 15 is provided for delivering pacing pulses to the patient's heart via electrodes 13 using programmable pacing parameters. HS signals are recorded during variation of selected pacing parameters to determine a hemodynamic response to changes in at least one pace parameters. The HS signal response to variation of a pace parameter is used to determine an optimal pace parameter setting for achieving hemodynamic benefit from the cardiac pacing therapy. Accordingly, pulse generator 15 is coupled to cardiac pace electrodes included in electrodes 13, which may include transvenous intracardiac electrodes, epicardial electrodes, and/or subcutaneous/submuscular electrodes or other transvenous or extravascular electrodes in the case of a neurostimulation delivered as a cardiac therapy. The electrodes 13 used for delivering pacing pulses may be dedicated pacing electrodes or may include shared pacing and sensing electrodes. Switching circuitry (not shown) may be used for selecting which electrodes 13 are coupled to ECG/EGM sensing circuitry 14 and which electrodes are coupled to pulse generator 15 as well as the polarity of such electrodes. While two electrodes are shown coupled to pulse generator 15 and two electrodes are shown coupled to ECG/EGM sensing module 14 in FIG. 1, it is recognized that multiple sensing and pacing channels corresponding to multiple heart chambers will require multiple electrodes coupled to each of sensing module 14 and pulse generator 15 and such connections may be controlled by a switching circuit, particularly when multipolar electrodes are positioned relative to a single heart chamber.

Pulse generator 15 is controlled by control processor 16 to deliver pacing pulses according to a test algorithm during which heart sounds are recorded for generating trends of a HS parameter with respect to the pace parameter. Control processor 16 receives signals from ECG/EGM sensing circuitry 14 for use in controlling pulse generator 15 to deliver appropriately timed pacing pulses. Appropriately timed pacing pulses are pulses that are typically delivered at a rate greater than an intrinsic depolarization rate such that the pacing pulses control the timing of heart chamber activation. As such, a lower pacing rate and/or a pacing timing interval such as an AV interval or VV interval may be controlled such that a pacing pulse precedes an intrinsic activation of the heart the majority of the time to maintain a desired heart rate and inter-chamber timing intervals. Appropriately timed pacing pulses are also delivered outside the vulnerable period of the heart to avoid risk of arrhythmia induction.

Control processor 16 may include any one or more of a microprocessor, a digital state machine, a digital signal processor (DSP), an application specific integrated circuit (ASIC), a field-programmable gate array (FPGA), or equivalent discrete or integrated logic circuitry. In some examples, processor 16 may include multiple components, such as any combination of one or more microprocessors, one or more controllers, one or more DSPs, one or more ASICs, or one or more FPGAs, as well as other discrete or integrated logic circuitry. The functions attributed to control processor 16 herein may be embodied as software, firmware, hardware or any combination thereof, implemented in a single device or distributed across two or more devices, which may include one or more implantable devices, external devices, or a combination of both.

Control processor 16 includes a HS analysis module 22 for analyzing heart sound signals obtains by HS sensing 12 to determine HS parameters. The HS parameters are used to determine an optimal setting for at least one pacing control parameter. HS analysis module 22 includes circuitry and/or computer-readable instructions for performing an algorithm for deriving HS parameters and trends or relative changes in HS parameters with a changing pace control parameter.

Memory 18 stores algorithms used by control processor 16 for performing pacing parameter optimization. Such algorithms may include pacing protocols used to obtain HS signals responsive to different pacing conditions. Memory 18 may also be used to store other data and information used by control processor 16 for controlling device functions, including a pacing or neurostimulation therapy delivered by pulse generator 15, controlling sensing functions by ECG/EGM sensing circuitry 14, controlling telemetry module 20, and controlling patient alert 24 in response to detecting an alert condition based on HS signals and/or cardiac electrical signals.

It is contemplated that IMD 10 may include or be coupled to other sensors 28 which provide signals to control processor 16 correlated to other physiological conditions of the patient. Sensors 28 may include an activity sensor, posture sensor, pressure sensor, oxygen sensor, temperature sensor, impedance sensor or the like. Sensor signals may be used by control processor 16 to detect a physiological condition of the patient indicating a need to provide or adjust therapy or generate a patient alert. In some embodiments, sensors 28 are used to determine control conditions, such as activity level and/or posture, during which a pace control parameter optimization procedure will be performed.

Telemetry module 20 is configured for bidirectional communication with an external programmer or computer operating software for programming the IMD 10. Control processor 16 may generate HS data and information relating to optimal pacing parameters that is transmitted to an external device via telemetry module 20 for review by a clinician. In some embodiments, functions attributed herein to control processor 16 may be performed across one or more processors that may include an external processor receiving data from telemetry module 20.

Figure 2:
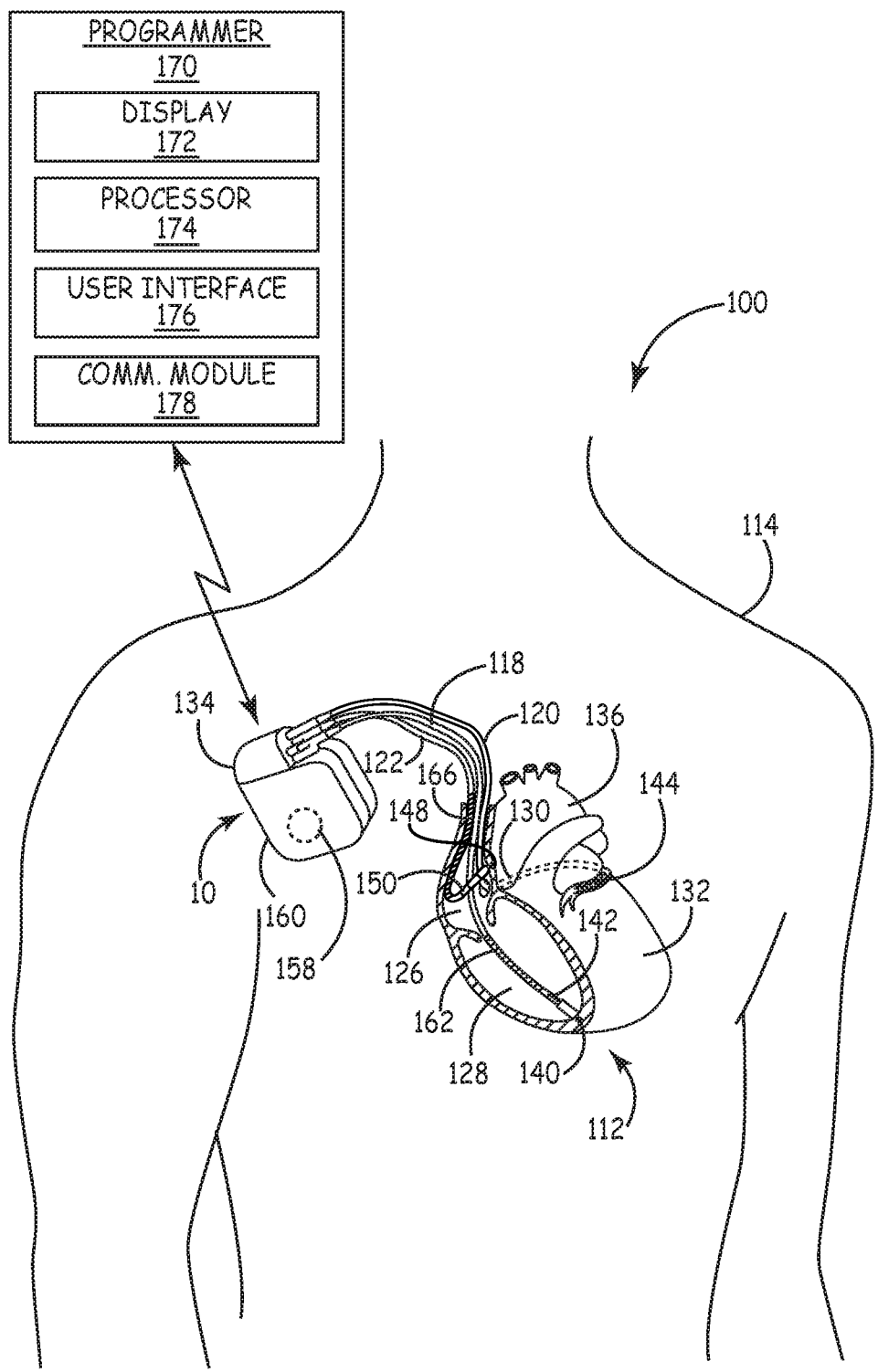
FIG. 2 is a schematic diagram of one embodiment of an implantable medical device (IMD) system in which techniques disclosed herein may be implemented to provide therapy to the heart of a patient.

FIG. 2 is a schematic diagram of one embodiment of an IMD system 100 in which techniques disclosed herein may be implemented to provide therapy to heart 112 of patient 114. System 100 includes IMD 10, shown by the functional block diagram of FIG. 1. IMD 10 is coupled to leads 118, 120, and 122 which carry multiple electrodes generally corresponding to electrodes 13 of FIG. 1. IMD 10 is configured for bidirectional communication with programmer 170. IMD 10 may be, for example, an implantable pacemaker, cardioverter, and/or defibrillator that provides electrical signals to heart 112 via electrodes coupled to one or more of leads 118, 120, and 122. IMD 10 is capable of delivering at least single chamber ventricular pacing, and in the embodiment shown, is configured for multi-chamber pacing and sensing in the right atrium (RA) 126, the right ventricle (RV) 128, and the left ventricle (LV) 132 using leads 118, 120 and 122.

IMD 10 delivers RV pacing pulses and senses RV intracardiac EGM signals using RV tip electrode 140 and ring electrode 142 positioned in the RV 128. RV lead 118 is shown to carry a coil electrode 162 which may be used for delivering high voltage cardioversion or defibrillation shock pulses. IMD 116 senses LV EGM signals and deliver LV pacing pulses using the electrodes 144 carried by multipolar coronary sinus lead 120, extending through the RA 126 and into a cardiac vein 130 via the coronary sinus. In some embodiments, coronary sinus lead 120 may include electrodes positioned along the left atrium (LA) 136 for sensing left atrial (LA) EGM signals and deliver LA pacing pulses.

IMD 10 senses RA EGM signals and delivers RA pacing pulses using RA lead 122, carrying tip electrode 148 and ring electrode 150. RA lead 122 is shown to be carrying coil electrode 166 which may be positioned along the superior vena cava (SVC) for use in delivering cardioversion/defibrillation shocks. In other embodiments, RV lead 118 carries both the RV coil electrode 162 and the SVC coil electrode 166. IMD 10 may detect arrhythmias of heart 112, such as fibrillation of ventricles 128 and 132, and deliver defibrillation therapy to heart 112 in the form of electrical pulses. While IMD 10 is shown in a right pectoral implant position in FIG. 2, a more typical implant position, particular when IMD 10 is embodied as an ICD, is a left pectoral implant position.

IMD 10 includes internal circuitry for performing the functions attributed to IMD 10 and a housing 160 encloses the internal circuitry. It is recognized that the housing 160 or portions thereof may be configured as an active electrode for use in cardioversion/defibrillation shock delivery or used as an indifferent electrode for unipolar pacing or sensing configurations. IMD 10 includes a connector block 134 having connector bores for receiving proximal lead connectors of leads 118, 120 and 122. Electrical connection of electrodes carried by leads 118, 120 and 122 and IMD internal circuitry is achieved via various connectors and electrical feedthroughs included in connector block 134.

In the embodiment shown, IMD 10 is also configured for delivering CRT therapy, which may use a selected pacing vector for LV pacing that includes at least one electrode 144 on multipolar LV lead 120. IMD 10 may be configured to pace in one or both ventricles 128 and 132 for controlling and improving ventricular synchrony. The methods described herein may be implemented in a single, dual or multi-chamber pacemaker or ICD delivering pacing pulses using programmable pacing pulse timing parameters and/or programmable pacing vectors, collectively referred to herein as "pace control parameters". Pace control parameter are not limited to timing-related parameter and pacing vector selections and may additionally include any control parameter used by the control processor 16 in controlling the delivery of pulses by pulse generator 15 (FIG. 1).

System 100 includes a HS sensor 158, which is shown to be incorporated within housing 160 of IMD 10. As described above, HS sensor 158 may be a microphone, accelerometer, e.g. a piezoelectric transducer sensitive to the vibrations caused by motion of the heart structures, or other acoustical sensor. In other embodiments, a HS sensor may be carried by an intra- or extravascular lead and is positioned in operative relation to heart 112 for obtaining signals representative of heart sounds.

IMD 10 may provide HS signal data to programmer 170 via wireless telemetry. HS data and/or a recommendation of one or more pace control parameter settings may be transmitted to programmer 170 for display to a user. Thus, the pace control optimization procedures described herein may be automated in the IMD system 100 and not require a specialized technician to perform the analysis, as required for example during echocardiography studies. The procedure may be performed automatically by IMD 10 with optimal pace control parameters identified and automatically programmed by IMD 10. The optimization procedure may alternatively be performed by IMD 10 with HS signal data and/or recommended pace control parameter setting(s) transmitted to programmer 170 for display to a user.

Programmer 170 includes a display 172, a processor 174, a user interface 176, and a communication module 178 including wireless telemetry circuitry for communication with IMD 10. In some examples, programmer 170 may be a handheld device or a microprocessor based home monitor or bedside programming device. A user, such as a physician, technician, nurse or other clinician, may interact with programmer 170 to communicate with IMD 10. For example, the user may interact with programmer 170 via user interface 176 to retrieve physiological or diagnostic information from IMD 10. A user may also interact with programmer 170 to program IMD 10, e.g., select values for operational parameters of the IMD. A user interacting with programmer 170 may request IMD 10 to perform a HS-based optimization algorithm and transmit results to programmer 170 or request data stored by IMD 10 relating to HS analysis procedures performed automatically by IMD 10 on a periodic basis. Processor 174 receives data from IMD 10 for use in generating a display presented on display 172 including information relating to HS data.

Programmer 170 includes a communication module 178 to enable wireless communication with IMD 10. Examples of communication techniques used by system 100 include low frequency or radiofrequency (RF) telemetry, which may be an RF link established via Bluetooth, WiFi, MICS, or as described in U.S. Pat. No. 5,683,432 "Adaptive Performance-Optimizing Communication System for Communicating with an Implantable Medical Device" (Goedeke, et al). In some examples, programmer 170 may include a programming head that is placed proximate to the patient's body near the IMD 10 implant site, and in other examples programmer 170 and IMD 10 may be configured to communicate using a distance telemetry algorithm and circuitry that does not require the use of a programming head and does not require user intervention to maintain a communication link.

It is contemplated that programmer 170 may be coupled to a communications network via communications module 178 for transferring data to a remote database or computer to allow remote management of a patient using the HS-based pacing parameter optimization techniques described herein. Remote patient management systems may be configured to utilize the presently disclosed techniques to enable a clinician to review HS data and authorize programming of IMD pace control parameters. For example, HS signals or parameters derived there from may be transferred from programmer 170 to a clinic or other expert center for review. Recommended pace control parameters may be authorized for programming in the IMD by a clinician or other expert then programmed using remote IMD programming techniques via a communications network and programmer 170. Reference is made to commonly-assigned U.S. Pat. No. 6,599,250 (Webb et al.), U.S. Pat. No. 6,442,433 (Linberg et al.) U.S. Pat. No. 6,622,045 (Snell et al.), U.S. Pat. No. 6,418,346 (Nelson et al.), and U.S. Pat. No. 6,480,745 (Nelson et al.) for general descriptions and examples of network communication systems for use with implantable medical devices for remote patient monitoring and device programming, all of which patents are hereby incorporated herein by reference in their entirety.

Figure 3:
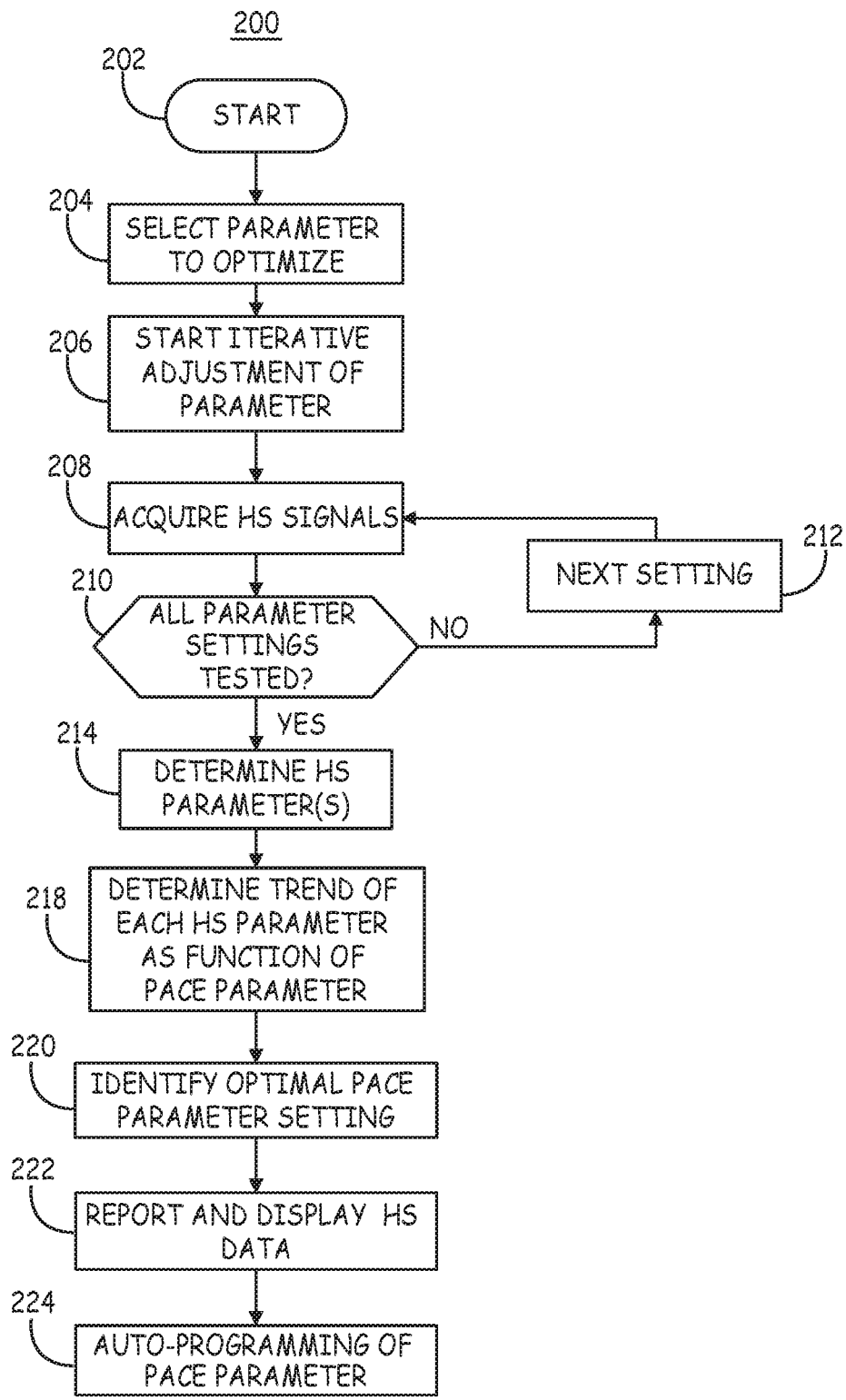
FIG. 3 is a flow chart of a method for optimizing pace control parameters according to one embodiment.

FIG. 3 is a flow chart 200 of a method for optimizing pace control parameters according to one embodiment. Flow chart 200 and other flow charts presented herein are intended to illustrate the functional operation of the medical device and should not be construed as reflective of a specific form of software or hardware necessary to practice the methods described. It is believed that the particular form of software will be determined primarily by the particular system architecture employed and by the particular sensing and pacing delivery methodologies employed by the device. Providing software, firmware and/or hardware in any combination to accomplish the described functionality in the context of any modern medical device system, given the disclosure herein, is within the abilities of one of skill in the art.

Methods described in conjunction with flow charts presented herein may be implemented in a computer-readable medium that includes instructions for causing a programmable processor included in the medical device system to carry out the methods described. A "computer-readable medium" includes but is not limited to any volatile or non-volatile media, such as a RAM, ROM, CD-ROM, NVRAM, EEPROM, flash memory, and the like. The instructions may be implemented as one or more software modules, which may be executed by themselves or in combination with other software.

A pace parameter optimization method is initiated at block 202. The optimization process may be initiated in response to a user command received via an external programmer. At a time of initial IMD implantation or during office follow-up visits, or during a remote patient monitoring session, a user may initiate a HS-base optimization procedure using an external programmer or networked computer. Additionally, or alternatively, the process shown by flow chart 200 may be an automated process started periodically or in response to sensing a need for therapy delivery or therapy adjustment based on a sensed physiological signal, which may include sensed HS signals.

At block 204 a pace control parameter to be optimized is selected. A control parameter may be a timing-related parameter, such as AV interval or W interval. Pacing vector is another control parameter that may be selected at block 204 for optimization. For example, when a multi-polar lead is used, such as the CS lead 120 shown in FIG. 2, multiple bipolar or unipolar pacing vectors may be selected for pacing in a given heart chamber. The pacing site associated with a particular pacing vector may have a significant effect on the hemodynamic benefit of a pacing therapy. As such, pacing vector is one pace control parameter that may be optimized using methods described herein.

A pacing sequence is initiated at block 206 using an initial parameter setting for the test parameter selected at block 204. In one embodiment, the AV interval is being optimized, and ventricular pacing is delivered at an initial AV interval setting. It is understood that an initial AV interval setting may be selected at block 206 by first measuring an intrinsic AV interval in a patient having intact AV conduction, i.e. no AV block. An initial AV interval may be a default pacing interval, the last programmed AV interval, or a minimum or maximum AV interval to be tested. Alternatively, if the VV interval is selected for optimization, an intrinsic inter-ventricular conduction time may be measured first and paced VV intervals may be iteratively adjusted beginning at a VV interval longer, shorter or approximately equal to the intrinsic VV conduction time.

An iterative process for adjusting the selected test parameter to at least two different settings is performed. The parameter may be adjusted to different settings in any desired order, e.g. increasing, decreasing, random etc. For example, during adjustment of AV interval, an initial AV interval may be set to just longer than or approximately equal to a measured intrinsic AV conduction time then iteratively decreased down to a minimum AV interval test setting. During pacing using each pace parameter setting, HS signals are acquired at block 208. The iterative process advances to the next test parameter setting at block 212 until all test parameter settings have been applied, as determined at block 210, and HS signals have been recorded for each setting.

HS signals may be acquired for multiple cardiac cycles to enable ensemble averaging or averaging of HS parameter measurements taken from individual cardiac cycles. It is understood that amplification, filtering, rectification, noise cancellation techniques or other signal processing steps may be used for improving the signal-to-noise ratio of the HS signals and these steps may be different for each of the heart sounds being acquired, which may include any or all of S1 through S4.

At least one HS parameter measurement is determined from the recorded HS signals for each test parameter setting at block 214. The IMD processor or an external processor, e.g. included in programmer 170, or a combination of both may perform the HS signal analysis described herein. In one embodiment, S1 and S2 are recorded and HS parameters are measured using the S1 and S2 signals at block 214. For example, the amplitude of S1, the V-S2 interval (where the V event may be a V pace or a sensed R-wave), and the S1-S2 interval are measured. The presence of S3 and/or S4 may additionally be noted or measurements of these signals may be made for determining related parameters. HS signal parameters are determined for at least two different test parameter settings, e.g. at least two different AV intervals, two or more different VV intervals, or two or more different pacing vectors.

At block 218, a trend for each HS parameter determined at block 210 as a function of the pace parameter test settings is determined. In one embodiment, a trend for each of the V-S2 interval, S1 amplitude and S1-S2 interval is determined. Other embodiments may include determining a separation of the M1 and T1 sounds during the S1 signal. Based on the trends of the HS parameter(s) with respect to the varied pace control parameter, an optimal pace parameter setting may be identified automatically by the processor at block 220. Additionally, or alternatively, the HS trends are reported and displayed at block 222 on an external device such as programmer 170 (in FIG. 2) or at a remote networked computer.

If the pace parameter being tested is, for example, pacing site or pacing vector when a multipolar electrode is positioned along a heart chamber, such as the quadripolar lead 120 along LV 132 shown in FIG. 2, a pacing site or vector may be selected based on maximizing a HS-based surrogate for ventricular contractility. In one embodiment, the amplitude of S1 is used as a surrogate for ventricular contractility, and a pacing site or vector associated with a maximum S1 is identified at block 220 as the optimal pacing vector setting.

Determining the trend of each HS parameter at block 218 may include determining whether the V-S2 interval trend presents a sudden slope change, e.g. from a substantially flat trend to a decreasing trend. An AV interval associated with a sudden change in the V-S2 interval trend may be identified as an optimal AV interval setting. The optimal AV interval may be further identified based on other HS trends, for example a maximum S1 amplitude and/or a maximum S1-S2 interval.

In some embodiments, an automatically-identified optimal pace parameter setting may also be automatically programmed in the IMD at block 224. In other embodiments, the clinician or user reviews the reported HS data and recommended pace parameter setting(s) and may accept a recommended setting or select another setting based on the HS data.

Figure 4:
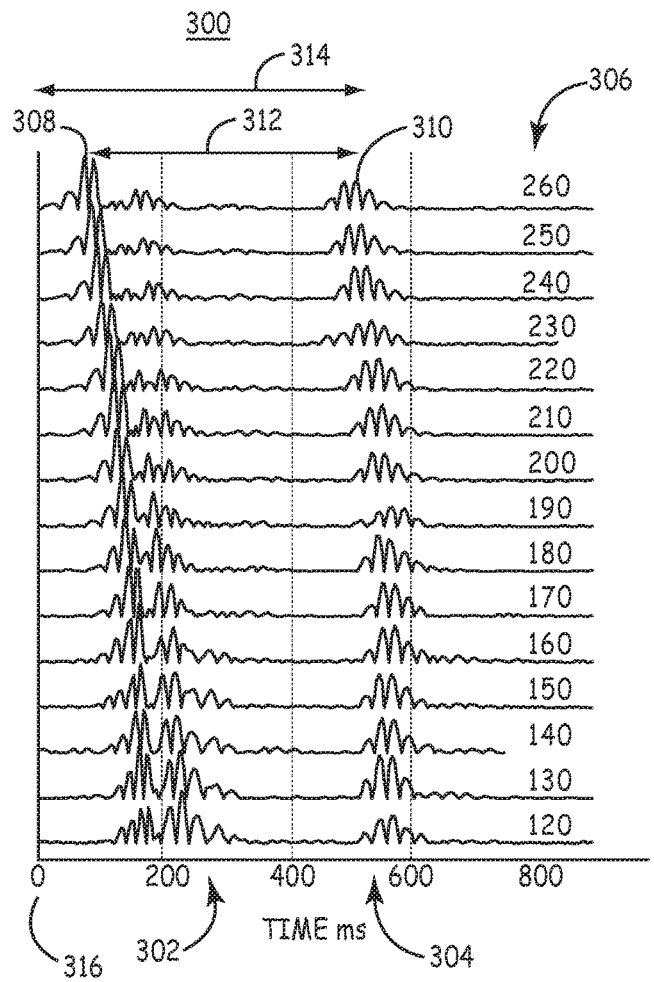
FIG. 4 is a display of HS signals recorded for varying AV interval settings.
Figure 5:
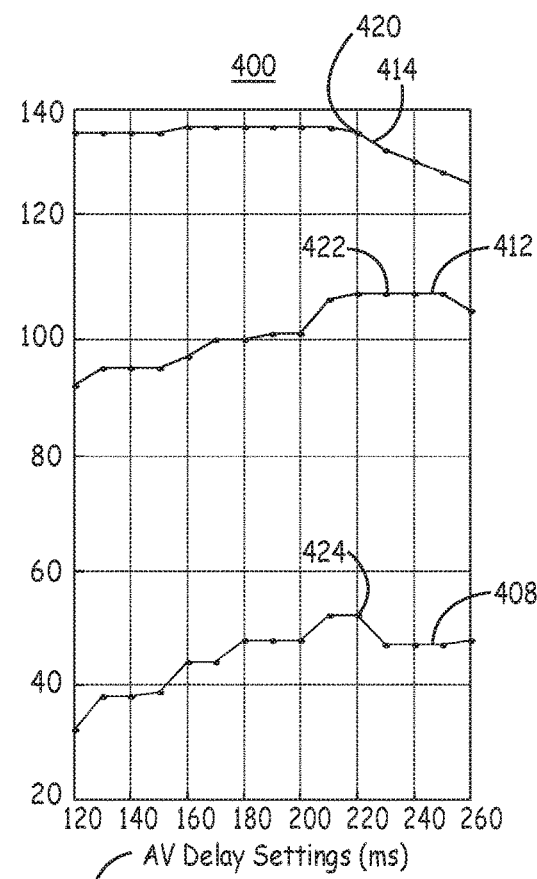
FIG. 5 is a plot of HS parameter trends generated from the data shown in FIG. 4.

FIGS. 4 and 5 show HS data that may be displayed, separately or combined, to a clinician or other user on programmer display 126 (FIG. 2) or on a remote networked computer. FIG. 4 is a display 300 of HS signals recorded for varying AV interval settings. The data shown in display 300 may be generated by the IMD processor and transmitted to an external programmer or networked computer for viewing by a clinician. Alternatively, the data may be generated from raw HS signal data by a processor included in an external programmer 170 or networked remote patient management system.

S1 signals 302 and S2 signals 304 recorded during pacing at different AV interval settings 306, ranging from 120 ms to 260 ms in this example, are displayed. The S1 and S2 signals 302 and 304 represent rectified and ensemble averaged signals obtained during approximately 10 seconds of pacing at the given AV interval setting. As can be observed on display 300, the amplitude and morphology of both S1 302 and S2 304 change with varying AV interval. Additionally, the S1-S2 time interval 312 changes with AV interval. The S1-S2 time interval 312 is shown as being measured between a detected maximum peak amplitude 308 and maximum peak amplitude 310 of each of the respective S1 302 and S2 signals 304. In various embodiments, different fiducial points may be defined for detection of S1 and S2 signals for determination of an S1-S2 time interval 312.

Time "0" 316 corresponds to the time of the ventricular pacing pulse. A V-S2 time interval 314 measured from the ventricular pacing pulse to the S2 peak 310 is also observed to change with different AV interval settings 306. The V-S2 time interval 314 may be measured as a time interval between an RV pacing pulse or sensed RV R-wave and the S2 peak amplitude 310, or an LV pacing pulse or sensed LV R-wave and S2 peak amplitude or another fiducial S2 signal point.

The HS parameters S1 peak amplitude 308, S1-S2 interval 312 and V-S2 interval 314 are determined for each AV interval setting 306. The trend of one or more of the HS parameters with AV interval is used for identifying an optimal AV interval.

FIG. 5 is a HS parameter plot 400 generated from the data shown in FIG. 4. The S1 amplitude trend 408, S1-S2 interval trend 412, and V-S2 interval trend 414 are each shown plotted as a function of AV interval 406 (also referred to herein as "AV delay"). As can be observed, the S1 amplitude trend 408 is generally bell-shaped having a peak at approximately 220 ms. S1-S2 interval trend 412 is generally increasing, reaching a peak at approximately 220 ms. The V-S2 interval trend 414 is flat with a sudden slope change to a decreasing trend at an inflection point 420 occurring at approximately 220 ms.

In one embodiment, a V-S2 interval trend that exhibits a sudden change, e.g. from a substantially flat trend to a suddenly decreasing trend, represents a patient that will benefit from AV interval optimization during CRT. When the V-S2interval trend 414 exhibits a sudden change, an optimal AV interval may be recommended as the AV interval at which the sudden change inflection point occurs. Furthermore, periodic optimization of the AV interval may be recommended in this patient.

In other embodiments, additional analysis of other HS parameters is performed to identify the optimal AV interval. For example, the AV interval at which the sudden change inflection point 420 occurs may be identified as an optimal AV interval. Longer AV intervals result in decreasing V-S2 interval which may be associated with a fusion period of atrial intrinsic conduction and ventricular pace induced conduction. The optimal AV delay may correspond to the lower boundary of the fusion band. In the given example, the lower boundary of the fusion band (i.e., the optimal AV interval) would be approximately 220 ms. One or more other HS parameters are then examined to determine an optimal AV interval at or less than 220 ms. For example, the S1-S2 interval trend 412 is observed to reach a maximum peak value 422 at both 220 ms and 240 ms. However, 220 ms is the first AV interval at which the peak occurs. As such, 220 ms is identified as the optimal AV interval. The S1 amplitude trend 408 may additionally or alternatively be examined to determine a maximum value that occurs at or below the optimal AV interval. In this example, the maximum S1 amplitude 424 correlates with a maximum S1-S2 interval 422 and the inflection point 420 defining a maximum AV interval based on a sudden inflection point of the V-S2 interval trend 414.

Figure 6:
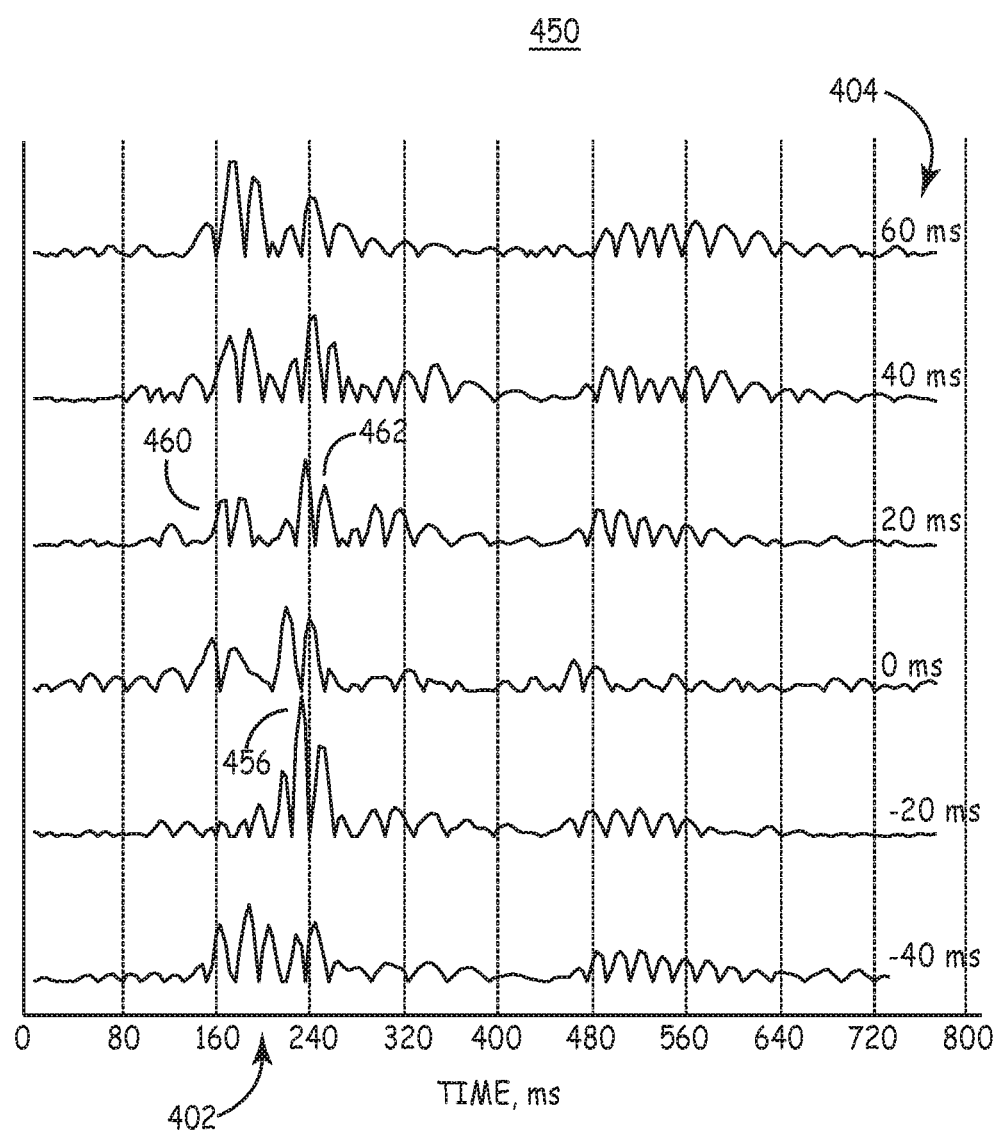
FIG. 6 is a display of HS signals recorded for varying VV interval settings during a VV interval optimization procedure.

FIG. 6 is a display 450 of HS signals recorded for varying VV interval settings 404 during a VV interval optimization procedure. As described above, data shown in display 450 may generated by the IMD processor and/or an external processor and displayed on a programmer or networked remote computer for review by a clinician. S1 signals 402 are shown for each of the VV interval settings 404. A setting of 0 ms results in simultaneous RV and LV pacing pulse delivery. A positive setting results in the LV being paced earlier than the RV, and a negative setting results in the RV being paced earlier than the LV. Thus, the VV interval setting corresponds to the timing of an LV pacing pulse relative to an RV pacing pulse.

The S1 amplitude 456 is observed to be maximized at a VV interval of −20 ms. This maximum S1 amplitude 456 is also observed to correspond to a merging of the M1 and T1 signals corresponding to closure of the mitrel and tricuspid valves, respectively compared to the S1 signal recorded for other VV intervals. For example, at a VV interval of 20 ms, the M1 signal 460 and the T1 signal 462 are observed to separate resulting in an overall lower S1 amplitude. A plot of the M1-T1 separation time and/or S1 amplitude as a function of VV interval may be generated similar to the plot shown in FIG. 5 for AV delay to allow a clinician or user to observe the trend of the HS parameters with respect to VV interval and facilitate selection of an optimal VV interval setting.

Figure 7:
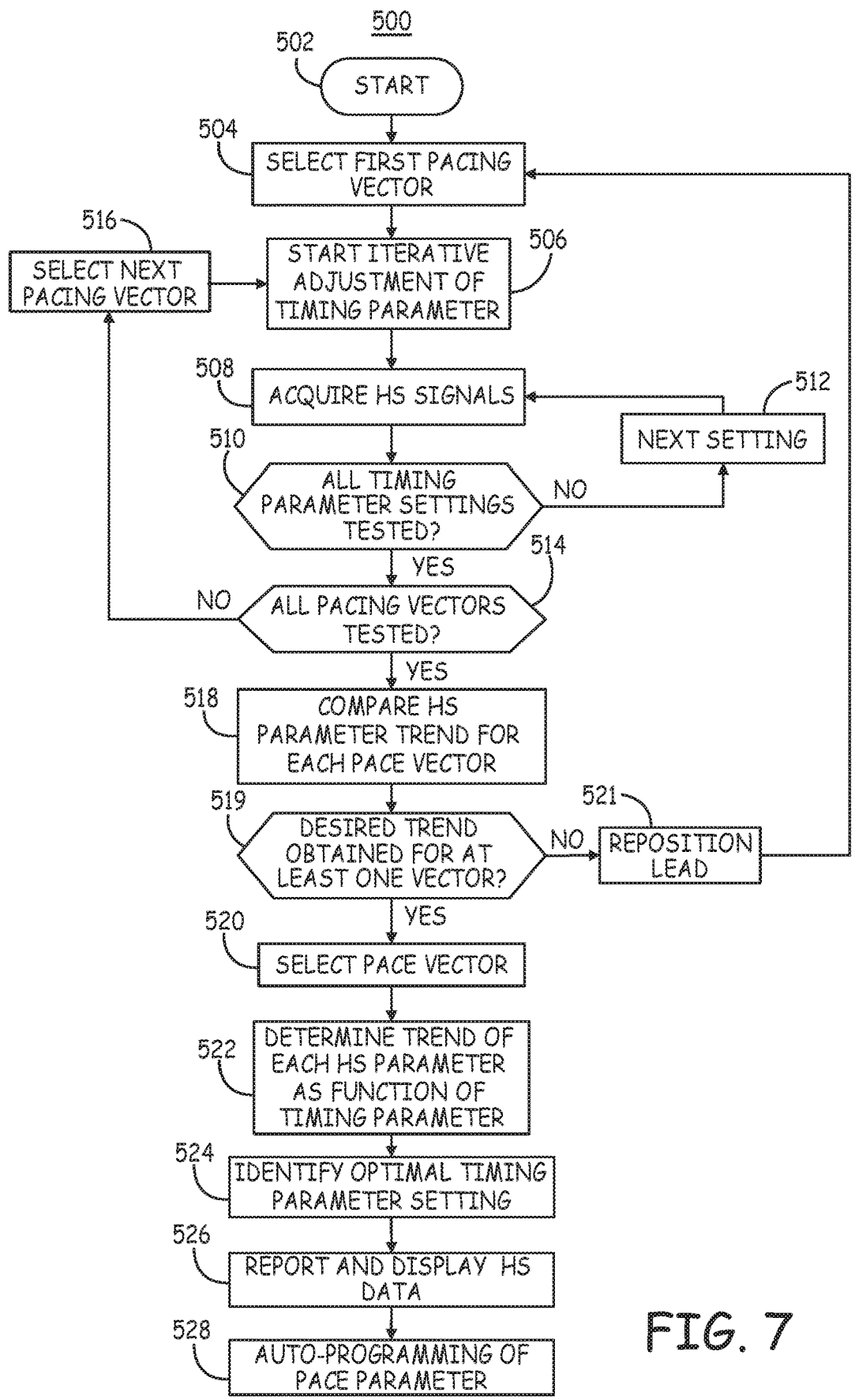
FIG. 7 is a flow chart of a method for selecting pace control parameters using HS signal analysis according to an alternative embodiment.

FIG. 7 is a flow chart 500 of a method for selecting pace control parameters using HS signal analysis. At block 502, the process is initiated, automatically or in response to a user command. The process may be initiated automatically on a periodic basis or triggered in response to another monitored signal, which may be a physiological signal such as an EGM or ECG, HS, pressure, oxygen, activity or posture signal. Other monitored signals or measurements which may trigger initiation of the process shown in flow chart 500 may include lead impedance measurements, capture threshold measurements, or detection of loss of capture.

The process shown in flow chart 500 is performed to identify an optimal pacing vector when multiple pacing vectors are available for pacing in a particular heart chamber. For example, in FIG. 2, a multi-polar lead is shown to include four electrodes 144 positioned for pacing in the LV 132. The four electrodes can be referred to as LV1 through LV4. At least sixteen bipolar pacing vectors are available using all bipolar combinations of electrodes 144 as well as at least four unipolar pacing vectors using each of electrodes 144 selected one at a time with an anode located away from the LV, such as an IMD housing electrode or RV coil electrode 162 or RV tip electrode 140. Different pacing sites corresponding to the location of each of electrodes LV1 through LV4 144 and different electrode vectors may produce different hemodynamic response to the pacing therapy.

At block 504, a first pacing vector is selected for testing from multiple pacing vectors available for pacing in a given heart chamber. At block 506, a pacing timing parameter, such as an AV interval or VV interval, is varied during pacing delivered using the selected pacing vector. HS signals are acquired for each pacing timing parameter setting at block 508, by advancing to a next timing parameter setting at block 512 until all timing parameter settings have been applied as determined at decision block 510.

In one embodiment, starting the iterative adjustment of the timing parameter at block 506 includes determining an initial setting based on historical data. For example, the IMD 10 may determine an intrinsic AV conduction time based on a sensed atrial P-wave and a sensed ventricular R-wave or an atrial pacing pulse and a sensed ventricular R-wave. The pacing history may also be used to determine a lower pacing rate during the iterative process. For example, a lower rate resulting in at least 90% atrial paced beats and an AV interval approximately equal to or just greater than the measured intrinsic AV conduction time may be set as the initial pace timing parameters at block 506. The AV interval is then iteratively reduced, e.g. by 20 ms decrements until a minimum AV interval test setting is reached. Each AV interval may be applied for a data acquisition time interval, for example 20 seconds or more, during which HS signals are acquired.

If all timing parameter settings have been tested, as determined at block 510, the next pacing vector is selected at block 516 until all test pacing vectors have been applied as determined at decision block 514. After obtaining HS signals for multiple settings of a pacing timing parameter for all test pacing vectors, a HS parameter trend with respect to the timing parameter is determined for each pacing vector. The HS parameter trends are compared between pacing vectors at block 518.

The HS trend with respect to timing parameter may present different behaviors between pacing vectors. For example, the trend may be generally flat for one vector and generally bell-shaped for another vector. In another example, the trend may be monotonically increasing or decreasing for one vector and having a sudden slope change for another vector. A particular trend may be indicative of a more favorable response to the pacing therapy. For example, if the HS parameter being evaluated is the V-S2 interval with respect to AV interval, a desired trend may include a sudden change in the trend, for example a sudden change from a generally flat trend to a decreasing trend. If the HS parameter being evaluated is S1 amplitude, a desired trend may be a generally bell-shaped curve having a recognizable peak.

If a desired trend indicating a positive hemodynamic response to the pacing therapy is not found for at least one pacing vector, as determined at decision block 519, the pacing lead may be repositioned at block 521 when the process shown by flow chart 500 is being performed during an initial implant procedure.

Alternatively, if the desired trend is not found, a default pacing vector or a vector having the next most favorable HS parameter trend may be selected. If the desired trend is observed for at least one vector, a vector having the desired trend is selected at block 520. For example, a pacing vector presenting a sudden change in the V-S2 interval trend with respect to AV interval may be selected. In another example, a pacing vector presenting a generally bell-shaped curve of the S1 amplitude may be selected. If more than one vector presents the desired trend, the vector presenting the greatest response of the HS parameter to the varying pace timing parameter may be selected, e.g. the greatest maximum peak of the HS parameter, greatest range of values, longest AV interval associated with a peak or inflection point, etc. Alternatively, if more than one vector presents the desired trend, additional HS parameters may be evaluated to select the optimal pacing vector at block 520.

At block 522, the trend of at least one HS parameter is evaluated as a function of the timing parameter for the selected pace vector. An optimal timing parameter setting is identified at block 524, for example using the methods described above. In one embodiment, a pace vector may be selected based on a trend of on HS parameter and then the trend of a different HS parameter may be used to determine an optimal timing control parameter. At block 526, a report of the HS data may be generated and displayed including trends of the measured HS parameters with respect to a pace control parameter. The selected pace vector and optimal timing parameter may be automatically programmed at block 528 or programmed by a user upon accepting the recommended values.

Thus, a medical device system and associated methods have been presented in the foregoing description with reference to specific embodiments. It is appreciated that various modifications to the referenced embodiments may be made without departing from the scope of the disclosure as set forth in the following claims.

The invention claimed is:

1. A method comprising:
    delivering, by a medical device system, pacing pulses at varying pacing settings;
    obtaining, by the medical device system, heart sound signals from an acoustical sensor;
    determining, by the medical device system and based on the heart sound signals, a plurality of heart sound signal parameters;
    determining, by the medical device system and based on the heart sound signal parameters, a relative change of a V-S2 interval, wherein the V-S2 interval is a time interval between a ventricular electrical event and an S2 heart sound, and wherein the relative change of the V-S2 interval is responsive to the varying pacing settings;
    identifying, by the medical device system and based on the relative change of the V-S2 interval, a target pacing parameter;
    delivering, by the medical device system, pacing pulses according to the target pacing parameter;
    deriving, by the medical device system, a trend of the V-S2 intervals with respect to the varying pacing settings; and
    displaying, by the medical device system, the trend of the V-S2 intervals with respect to the varying pacing settings.

2. The method of claim 1 wherein the varying pacing settings comprises a plurality of pacing vectors.

3. The method of claim 2 wherein the plurality of pacing vectors are selected from a plurality of electrodes positioned along a chamber of a heart.

4. The method of claim 2 wherein an optimal pacing vector is selected from the plurality of pacing vectors.

5. The method of claim 1 wherein the varying pacing settings comprises a plurality of pacing sites along a chamber of a heart.

6. The method of claim 5 wherein the chamber of the heart comprises a left ventricle.

7. The method of claim 5 wherein the plurality of electrodes are positioned along a distal end of a multi-polar lead.

8. The method of claim 7 wherein a proximal end of the multi-polar lead is coupled to the implantable medical device system.

9. The method of claim 5 wherein an optimal pacing site is selected from the plurality of pacing sites.

10. The method of claim 1 the implantable medical device system comprising an implantable pacemaker, cardioverter, or defibrillator.

11. The method of claim 1 further comprising:
    responsive to obtaining heart sound signals, recording, by the medical device system, heart sound signals for varying pacing settings.

12. The method of claim 1 wherein the varying pacing settings comprises one of interventricular (VV) interval settings, and atrial-ventricular (AV) interval settings.

13. A medical device system comprising:
    therapy delivery circuitry;
    an acoustical sensor; and
    processing circuitry, coupled to an external display, the processing circuitry configured to:
        control delivery of pacing pulses by the therapy delivery circuitry at varying pacing settings, obtain heart sound signals from the acoustical sensor, determine, based on the heart sound signals, a plurality of heart sound signal parameters, determine, based on the heart sound signal parameters, a relative change of a V-S2 interval, wherein the V-S2 interval is a time interval between a ventricular electrical event and an S2 heart sound, and wherein the relative change of the V-S2 interval is responsive to the varying pacing settings, identify, based on the relative change of the V-S2 interval, a target pacing parameter, control delivery of pacing pulses at the target pacing parameter, and derive a trend of the V-S2 interval with respect to the varying pacing settings, wherein the external display configured to present a trend of the V-S2 interval with respect to pacing settings.

14. The medical device system of claim 13 wherein the varying pacing settings comprises a plurality of pacing vectors.

15. The medical device system of claim 14 wherein the plurality of pacing vectors are selected from a plurality of electrodes positioned along a chamber of a heart.

16. The medical device system of claim 15 wherein the plurality of electrodes are positioned along a distal end of a multi-polar lead.

17. The medical device system of claim 16 wherein a proximal end of the multi-polar lead is coupled to the implantable medical device system.

18. The medical device system of claim 14 wherein an optimal pacing vector is selected from the plurality of pacing vectors.

19. The medical device system of claim 13 wherein the varying pacing settings comprises a plurality of pacing sites along a chamber of a heart.

20. The medical device system of claim 19 wherein the chamber of the heart comprises a left ventricle.

21. The medical device system of claim 19 wherein an optimal pacing site is selected from the plurality of pacing sites.

22. The medical device system of claim 13 comprising an implantable pacemaker, cardioverter, or defibrillator comprising the therapy delivery circuitry.

23. The medical device system of claim 13 wherein the processing circuitry is configured to:
    responsive to obtaining heart sound signals, record heart sound signals for varying pacing settings.

24. The medical device system of claim 13 wherein the varying pacing settings comprises one of interventricular (VV) interval settings, and atrial-ventricular (AV) interval settings.

25. A method comprising:
    delivering, by a medical device system, pacing pulses at varying pacing settings;
    obtaining, by the medical device system, electrical signals indicative of ventricular events and heart sound signals from an acoustical sensor;
    determining, by the medical device system based on the electrical signals and the heart sound signals, a relative change of V-S2 intervals, wherein the V-S2 intervals are time intervals between the ventricular events and subsequent S2 heart sounds, and wherein the relative change of the V-S2 intervals is responsive to the varying pacing settings;
    identifying, by the medical device system and based on the relative change of the V-S2 intervals, a target pacing parameter;
    delivering, by the medical device system, pacing pulses according to the target pacing parameter;

deriving, by the medical device system, a trend of the V-S2 intervals with respect to the varying pacing settings; and displaying, by the medical device system, the derived trend.

26. A method comprising:

delivering, by a medical device system, pacing pulses at varying pacing settings;

obtaining, by the medical device system, electrical signals indicative of ventricular events and heart sound signals from an acoustical sensor;

determining, by the medical device system based on the heart sound signals, a plurality of heart sound signal parameters;

determining, by the medical device system based on the electrical signals and the heart sound signals, a relative change of V-S2 intervals, wherein the V-S2 intervals are time intervals between the ventricular electrical events and subsequent S2 heart sounds, and wherein the relative change of the V-S2 intervals is responsive to the varying pacing settings;

identifying, by the medical device system and based on the relative change of the V-S2 intervals, a target pacing parameter;

delivering, by the medical device system, pacing pulses according to the target pacing parameter;

deriving, by the medical device system, a trend of at least one of the heart sound signal parameters with respect to the varying pacing settings; and displaying, by the medical device system, the derived trend.

\* \* \* \* \*